US00PP10148P

United States Patent [19]

Benardella

[11] Patent Number: Plant 10,148

[45] Date of Patent: Dec. 16, 1997

[54] HYBRID TEA ROSE PLANT NAMED 'BENRAAR'

[75] Inventor: Frank Benardella, Old Tappan, N.J.

[73] Assignee: DeVor Nurseries, Inc., Watsonville, Calif.

[21] Appl. No.: 708,259

[22] Filed: Sep. 6, 1996

[51] Int. Cl.[6] ..... A01H 5/00

[52] U.S. Cl. ..... Plt./13

[58] Field of Search ..... Plt./11, 13

[56] References Cited

PUBLICATIONS

"Modern Roses 8, The International Check–List of Roses", 1980, The McFarland Company, Harrisburg, Pennsylvania, p. 375.

*Primary Examiner*—Howard J. Locker

*Attorney, Agent, or Firm*—Christie, Parker & Hale, LLP

[57] ABSTRACT

A new Hybrid Tea rose plant producing flowers of red and white striped coloration.

1 Drawing Sheet

SUMMARY OF THE INVENTION

The present invention relates to a new and distinct variety of rose plant of the Hybrid Tea rose class which was originated by my crossing as seed parent the variety known as 'Picasso' (U.S. Plant Pat. No. 3,351) and as pollen parent an unnamed and unpatented seedling of my creation. The varietal denomination of this new rose is 'Benraar'.

Among the novel characteristics possessed by this new variety which distinguish it from its parents and all other varieties of which I am aware are its unusual and striking dual-colored red and white striped flowers.

Asexual reproduction by budding of the new variety as performed in Watsonville, Calif. shows that the foregoing and other distinguishing characteristics come true to form and are established and transmitted through succeeding propagations.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DETAILED DESCRIPTION OF THE NEW VARIETY

Parentage: Seedling.

*Seed parent.*—'Picasso'.

*Pollen parent.*—Unnamed seedling.

Class: Hybrid Tea.

The following is a detailed description of my new variety, of specimens grown under glass in Watsonville, Calif. in the month of August. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

Flower

Blooming habit: Continuous.

A. Bud:

(1) *Size.*—Small.

(2) *Form.*—Ovoid base.

(3) *Color.*—Before sepals separate and fall, bud color is near 58B to 60D.

(4) *Sepals.*—Sepals cover bud when tight then spread upon opening of bud, after which they reflex. Color: Near 144A, small white hairs on inside edges.

(5) *Peduncle.*—Length: About 10 cm. Aspect: Slightly curved. Strength: Erect, sturdy. Color: Near 144A.

(6) *Bracts.*—From single to 3 leaflet; number 0–2; elliptical, acute, about 10 cm from calyx.

B. Bloom:

(1) *Size.*—Average size when fully expanded — about 9–11 cm.

(2( *Borne.*—Singly, one to a stem.

(3) *Form.*—High centered, petals loosely rolled outward at maturity.

(4) *Petalage.*—Number of petals under normal conditions — about 43–46.

(5) *Color (⅓ to ½ open).*—Outer petals: Top surface near 57C to 58C-D with stripe of white near 155C-D; center near 57D to 58C-D with stripe of white near 155C-D and base near 4D. Undersurface near 63C with stripe of white near 155A and outer edge near 57A; center near 64D with stripe near 4D; base near 2C. Inner petals: Top surface near 155A with stripe of near 64C; center near 159C and base near 3C with near 64C. Undersurface near 57B with stripe of white near 155A-D; center near 57C with near 155B and base near 2C. The base of petals at point of attachment is near 2C and the general tonality from a distance is medium pink.

(6) *Color (fully open).*—Outer petals: Top surface near 58D with stripe of near 155D; center near 58D with stripe of near 155D and base near 158A. Undersurface near 61C with small patches of white near 155C; center near 57D; base near 1D. Inner petals: Top surface near 58D variegated with near 73D; center near 62A with white near 155B; base near 160C. Undersurface near 63B with streaks of white near 155B; center near 58C with near 155B and base near 158A. The base of petals at point of attachment is near 158A and the general tonality from a distance is medium pink.

(7) *Color change.*—As bloom ages the color lightens to a medium pink; white areas have a hint of yellow. Petal top surface near 63C; petal undersurface near 58C and general tonality at a distance medium pink.

C. Petals:

(1) *Texture.*—Thick.

(2) *Appearance.*—Inside leathery; outside smooth.

(3) *Form.*—Orbicular.

(4) *Arrangement.*—Imbricated, regularly arranged.
(5) *Petaloids.*—Usually 5 to 8.
(6) *Fragrance.*—Moderate.
(7) *Lasting quality.*—On plant — very long; about 10 to 14 days as cut flower.
(8) *Persistence.*—Petals persist.

Reproductive Organs

A. Stamens:
(1) *Arrangement.*—Irregular.
(2) *Anthers.*—Color — near 164A.
(3) *Filaments.*—Color — near 155B.
(4) *Pollen.*—Color — near 11B.

B. Pistils:
(1) *Styles.*—Scattered, uneven.
(2) *Stigmas.*—Color — near 11B.

C. Characteristics of hips: Not observed.

Plant

A. Form: Upright, compact.
B. Growth: Vigorous, uniform branching.
C. Foliage: Compound 3, 5 and 7 leaflets.
(1) *Size.*—Medium.
(2) *Quantity.*—Abundant.
(3) *Color.*—New foliage: Upper side — near 137A. Underside — near 176B. Old foliage: Upper side — near 147A. Underside — near 138B.
(4) *Shape.*—Oval with acute tip.
(5) *Texture.*—Upper side — semi-glossy; underside — leathery, dull.
(6) *Edge.*—Serrated.
(7) *Serration.*—Serrate.
(8) *Leaf stem.*—Color — medium green.
(9) *Stipules.*—Small, slender, curved inward.
(10) *Rachis.*—With prickles.
(11) *Petioles.*—Top near 137B; underside near 147B.
(12) *Auricle.*—Long, pointed.
(13) *Resistance to disease.*—Very good to blackspot; good to mildew; very good to rust.

D. Wood:
(1) *New wood.*—Color — new shoots near 185C. Bark — smooth.
(2) *Old wood.*—Color — near 137C. Bark — smooth.

E. Flower stem: About 60–95 cm from last cut.

F. Thorns:
*Quantity (main stalk).*—Few.
*On laterals from stalk.*—Few.
*Form.*—Slightly curved downward.
*Length.*—Medium.
*Color.*—Near 165B when young.
*Position.*—Regular.
*Prickles.*—Few.

F. Winter hardiness: Under greenhouse conditions in Watsonville, winters very well.

I claim:

1. A new and distinct variety of rose plant of the Hybrid Tea rose class, substantially as shown and described.

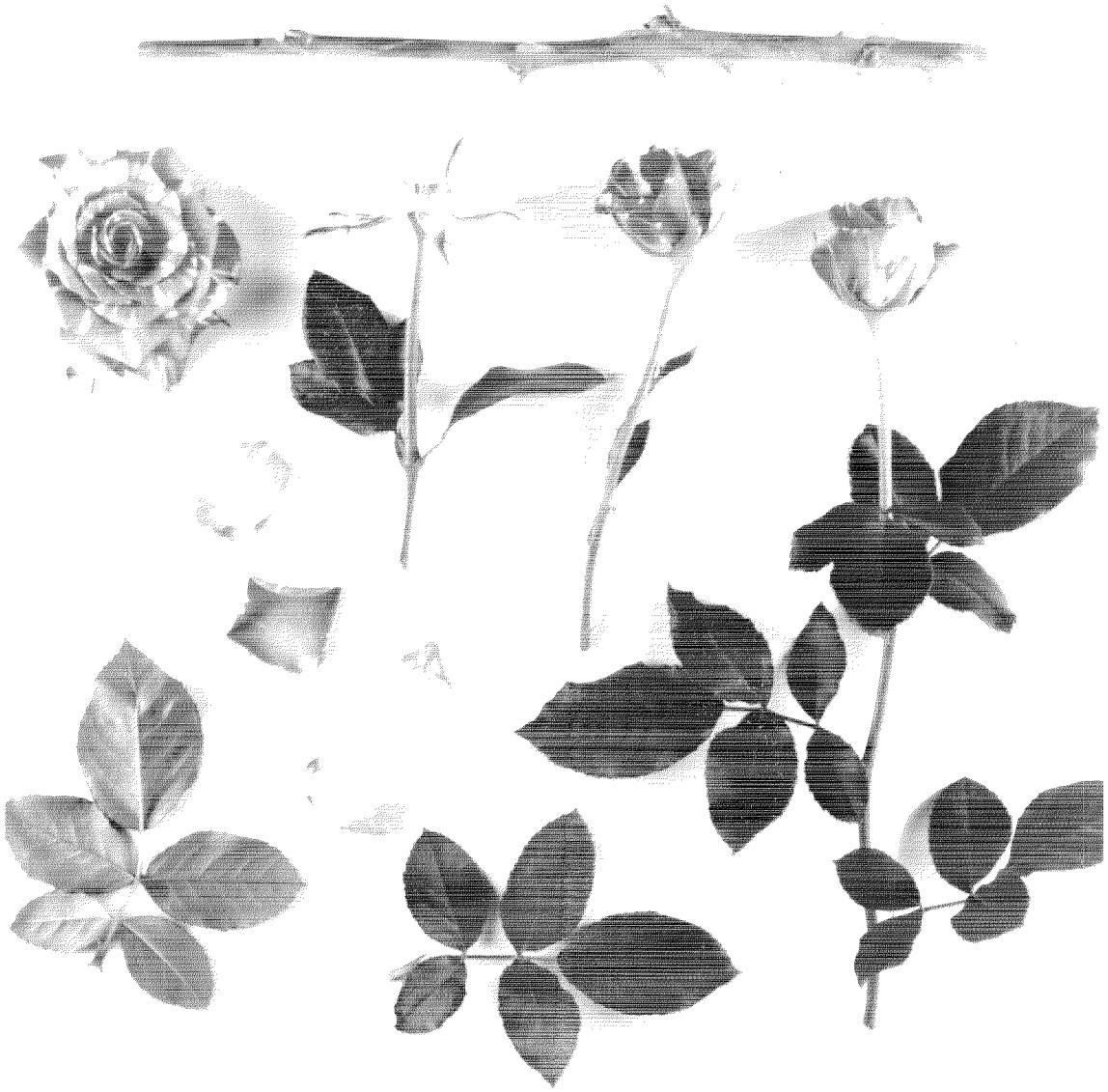

* * * * *